US009901519B2

(12) United States Patent
Neffgen et al.

(10) Patent No.: US 9,901,519 B2
(45) Date of Patent: Feb. 27, 2018

(54) INFILTRANT FOR DENTAL CERAMICS

(71) Applicant: Muhlbauer Technology GmbH, Hamburg (DE)

(72) Inventors: Stephan Neffgen, Pinneberg (DE); Ulrich Lohbauer, Nuremberg (DE)

(73) Assignee: MUHLBAUER TECHNOLOGY GmbH, Hamburg (DE)

( * ) Notice: Subject to any disclaimer, the term of this patent is extended or adjusted under 35 U.S.C. 154(b) by 23 days.

(21) Appl. No.: 14/904,249

(22) PCT Filed: Jul. 14, 2014

(86) PCT No.: PCT/EP2014/065044
§ 371 (c)(1),
(2) Date: Jan. 11, 2016

(87) PCT Pub. No.: WO2015/007686
PCT Pub. Date: Jan. 22, 2015

(65) Prior Publication Data

US 2016/0128908 A1 May 12, 2016

(30) Foreign Application Priority Data

Jul. 16, 2013 (EP) .................................... 13176738

(51) Int. Cl.
*A61K 6/08* (2006.01)
*A61K 6/083* (2006.01)
*A61K 6/00* (2006.01)

(52) U.S. Cl.
CPC ............ *A61K 6/083* (2013.01); *A61K 6/0002* (2013.01)

(58) Field of Classification Search
CPC ..................................................... A61K 6/083
See application file for complete search history.

(56) References Cited

U.S. PATENT DOCUMENTS

| | | | | |
|---|---|---|---|---|
| 5,091,033 | A * | 2/1992 | Nakabayashi | C09J 4/00 156/316 |
| 5,676,745 | A * | 10/1997 | Kelly | A61L 27/44 106/35 |
| 2006/0264532 | A1 | 11/2006 | Meyer-Luckel et al. | |
| 2010/0240853 | A1* | 9/2010 | Neffgen | A61K 6/083 526/328 |
| 2013/0116384 | A1 | 5/2013 | Neffgen et al. | |

FOREIGN PATENT DOCUMENTS

| | | |
|---|---|---|
| DE | 2145613 | 1/2010 |
| DE | 202012011045 | 2/2014 |

OTHER PUBLICATIONS

International Search Report and Written Opinion for PCT/EP2014/065044, dated Oct. 20, 2014, 8 pages.

* cited by examiner

*Primary Examiner* — Michael Pepitone
(74) *Attorney, Agent, or Firm* — Casimir Jones, S.C.; Mary Ann D. Brow

(57) ABSTRACT

An infiltrant comprising from 90 to 99.9 wt.-% of at least one polymerizable monomer, oligomer or prepolymer and from 0.05 to 10 wt.-% of a polymerization initiator, the infiltrant having a dynamic viscosity of 0.3 to 100 mPa·s (23° C.); for use in a method for strengthening a fixed ceramic dental prosthesis in the oral cavity.

15 Claims, No Drawings

INFILTRANT FOR DENTAL CERAMICS

This application is a § 371 US National Entry of International Application No. PCT/EP2014/065044, filed Jul. 14, 2014, which is incorporated herein by reference in its entirety, and which claims the benefit of European Application No. 13176738.6, filed Jul. 16, 2013.

Dental prostheses are highly stressed during use. Typically, damage is induced by wear processes but sometimes by the dentist, e.g. while adjusting occlusion, e.g. by using a bur just after having fixed the prosthesis. In particular, permanent fixed prosthesis parts made from ceramics thereby form damaged areas. A damaged area can be identified by its rougher surface compared to the surrounding ceramic surface. Damaged area means in particular a surface layer exhibiting micro cracks and/or micro pits. Damaged areas are characterized by a propagating weakened layer of the ceramic material. A damaged area decreases the lifetime of a dental ceramic prosthesis, e.g. by accelerating crack growth and fracture. A dentist today has no means or methods available to improve the strength and durability of a fixed prosthesis or to restore a damaged area of a fixed prosthesis in the oral environment. It was thus an aim of the present invention to provide means and methods for improving the strength and durability and/or for restoring surface areas of intraoral fixed ceramic prosthetic parts. Surprisingly, it was found that the provided means and methods according to the invention are suitable to completely or almost completely restore the tensile strength of a ceramic body. The provided means and methods are effective, convenient and time efficient to the patient and to the dentist.

Propagating weakened layers are a particular problem when silicate based ceramics, such as feldspathic ceramic or glass ceramic, are used.

In dentistry currently the best yet insufficient mode to treat roughened surface areas of ceramic prosthetic restorations is to polish the respective surface areas. However, by polishing a damaged or weakened area of a ceramic the original strength may not be achieved.

European Patent Application EP 2145613 A1 is related to infiltrants with high penetration coefficients for treating or preventing carious enamel lesions comprising crosslinking monomers, wherein at least 5% by weight of crosslinking monomers comprise at least three polymerizable groups. European Patent Application EP 2145613 A1 teaches further, that the fraction of crosslinking monomers having at least three polymerizable groups and a distance between crosslinking points of less than 10 bond lengths, based on the total mass of the monomers, is preferably less than 20% by weight, more preferably less than 10% by weight, more preferably less than 5% by weight.

European Patent EP 2226061 B1 describes infiltrants with high penetration coefficients for treating or preventing carious enamel lesions comprising crosslinking monomers and acidic monomers containing phosphoric and/or phosphoric acid groups.

It was an aim of the present invention to provide compositions, kits and methods for restoring damaged or weakened intraoral fixed ceramic prosthetic parts to restore at least the original strength and/or at least to increase the durability thereof.

Further it was an aim of the present invention to provide compositions, kits and methods for increasing the strength and/or durability of intraoral fixed ceramic prosthetic parts, in particular of damaged or weakened intraoral fixed ceramic prosthetic parts.

The present invention is defined in the claims.

Surprisingly, it was found that the provided compositions, kits and methods are suitable to restore at least the original tensile strength or flexural strength of a ceramic body.

Further surprisingly, it was found that the provided compositions, kits and methods are suitable to improve the tensile strength or flexural strength of a ceramic body, in particular of damaged or weakened intraoral fixed ceramic prosthetic parts.

The provided compositions, kits and methods are especially suitable for strengthening of silicate based ceramics after deterioration of the ceramic surface by mechanical processes, e.g. abrasive wear.

The invention provides an infiltrant comprising from 90 to 99.9 wt.-% of at least one polymerizable monomer, oligomer or prepolymer and from 0.05 to 10 wt.-% of a polymerization initiator, the infiltrant having a dynamic viscosity of 0.3 to 100 mPa·s (23° C.); for use in a method for strengthening a fixed ceramic dental prosthesis in the oral cavity The method preferably comprises the following steps:

a. optionally cleaning of a ceramic surface layer of the fixed prosthesis,
b. optionally rinsing of the ceramic surface layer
c. drying of the ceramic surface layer,
d. applying onto the dried ceramic surface layer the infiltrant,
e. optionally cleaning the surface of the ceramic surface layer from adherant infiltrant;
f. curing the infiltrant in the ceramic surface layer,
g. optionally cleaning and/or polishing the surface of the ceramic surface layer.

Preferably one of the first method steps is identifying a damaged or degraded ceramic surface. Identification can be carried out by visual and/or tactile inspection or by Optical Coherence Tomography (OCT). Optical Coherence Tomography (OCT) is preferred since an exact three-dimensional image of a damaged ceramic layer is available.

Another embodiment of the invention is to provide a kit, comprising:

a. an organic solvent having an Evaporation Index of 1 to 35, preferably 1 to 15,
b. an infiltrant according to any of the claims 1 to 7.

The first kit component comprises a drying agent, which consists essentially of an organic liquid having an Evaporation Index of 1 to 35. The kit component container comprises preferably an application device, in particular a brush, a cannula or a tip.

The second kit component comprises an infiltrant according to the invention. The kit component container comprises preferably an application device, in particular a brush, a cannula or a tip.

It was assumed by the inventors that penetrating oral liquids promote the progression of a once damaged layer. The attempt that was made therefor was to prevent the progression by sealing the damaged layer durably.

The approach was to completely infiltrate existing micro-cracks and/or micro-pits with infiltrants which have excellent penetration behavior and to seal micro-cracks and micro-pits below the surface after the infiltrant is cured.

Surprisingly, the experiments showed that not only a progress of the weakening was prevented, but also the weakened structure itself could be restored.

In particular, the strength (in particular, the resistance to fracture) of the ceramic was improved, restored or even improved compared to the initial strength or the strength after polishing away a weakened layer area.

In one embodiment the Infiltrant consists essentially of a mixture of monomers, oligomers or pre-polymers which have more than one polymerizable moiety and additives for curing.

Preferably the infiltrant is curable by radical polymerization.

In another embodiment the infiltrant consists essentially of a mixture of monomers, oligomers or pre-polymers which have more than one polymerizable moiety and a small percentage of monomers, oligomers or pre-polymers which have a silanol moiety and additives for curing.

Infiltrant means a composition that flows into micro pits and/or micro cracks of a solid body and fill in the pits and cracks within a few seconds and can be cured therein. The pits and cracks thereby have sizes in the range of a few microns to a few nanometers. Infiltrant further means a curable or more precisely a polymerizable liquid or more precisely solution comprising polymerizable monomers or a mixture of different polymerizable monomers, oligomers or prepolymers and additives dissolved in the monomers or monomer mixture. In the context of the invention the term infiltrant defines a mixture, being liquid at room temperature (23° C.) containing monomers, polymerization initiators and/or inhibitors and/or other additives necessary to at least keep the infiltrant manageable for the shelf life of the infiltrant. Monomer, oligomer or pre-polymer means a molecule which has at least one polymerizable moiety such as a vinyl group. Monomers, oligomers or pre-polymers which have more than one polymerizable moiety can function as cross linking agent. The infiltrants are Newtonian fluids. The infiltrant preferably has a dynamic viscosity at room temperature (RT) of 0.3 to 30 mPa*s. In another embodiment the infiltrant has a dynamic viscosity of at room temperature (RT, 23° C.) of 30 to 100 mPa·s.

Ceramic means a solid predominantly inorganic body, obtained by sintering at a certain temperature for a given period. Fixed ceramic prosthesis (part) means permanently fixed, in particular it means bonded or cemented and/or screwed to dental hard tissue or to a synthetic support.

A silicate based ceramic should be understood as a ceramic based on or containing major amounts of silicates. In the dental field silicate ceramics used are high glass content ceramics based on aluminosilicate glass [J. R. Kelly, JADA 2008, 139, suppl 4, 4S-7S] e.g. feldspathic ceramics, leucite- and mica based ceramics or high melting glass ceramics.

Another class of silicate based ceramics is structural ceramic with low glass content such as lithium disilicate ceramics, glass infused metal oxides or glass infused spinells and the like.

The present invention is useful especially for the treatment of a surface of a ceramic which is permanently fixed to a tooth, or which is permanently mounted in the oral cavity, such as to a dental implant. Such ceramic body can be an inlay, onlay, veneer, partial crown, crown, bridge, larger fixed prosthetic or the like. The prosthetic is made in total or in part of ceramic material. The ceramic part has directed to the oral cavity at least one surface, which is an oral, vestibular, occlusal, incisal or approximal surface.

The present invention may especially be applied to all kinds of silicate ceramic surfaces, in particular to all kinds of silicate ceramics fixed in the mammal body for medical and especially dental reasons.

The cleaning in step a. of the inventive method means at least the cleaning of the area of the ceramic prosthesis that has been damaged. Cleaning means removal of e.g. plaque and other adherent contaminants and can be performed by conventional dental treatment, e.g. polishing using abrasive pastes or air abrasion or using dental instruments or machines.

The rinsing in step b. of the inventive method can be performed by conventional dental treatment, e.g. with air-water spray or water alone.

The drying in step c. of the inventive method can be performed by applying a stream of dried air for a certain period—until it can be assumed that water or aqueous residues substantially have evaporated from existing pits and cracks. Preferably drying is performed by purging with an organic liquid. A suitable organic liquid is volatile in its entirety; preferably it has an Evaporation Index of 1 to 35, preferably of 1 to 15, wherein Evaporation Index means the evaporation time of the organic liquid divided by the evaporation time of acetone under the same conditions. The Evaporation Index (in German: Verdunstungszahl) can be identified according to "Deutsche Industrie Norm" DIN 53170:2009. Such a volatile organic liquid quickly evaporates in the oral cavity and thereby carries away residual water molecules. This drying can be done by simply injecting one or more times the liquid from a syringe onto the ceramic surface. The liquid is allowed to evaporate. Preferably the evaporation of the solvent is further accelerated and/or followed by applying a stream of dry air. The volatile organic liquid has preferably an initial boiling point between 35° C. and 100° C., preferably between 50° C. and 80° C. The organic liquid is preferably fully miscible with water. The organic liquid contains preferably no water or less than 5 percent by weight of water. The most preferred organic liquid is Ethanol or a mixture of Ethanol with other organic solvents.

Applying an infiltrant in step d. of the inventive method can be performed simply by bringing the infiltrant in contact with the ceramic surface, e.g. by using a cannula tip, a syringe, a brush or other suitable application systems, e.g. a sandwich composite foil having channels therein, with an proximal opening to the ceramic surface.

Curing of the infiltrant in step f. of the inventive method can be performed by exposure of the area to actinic radiation, using common dental polymerization lamps, most preferably with an emission maximum from 350 to 500 nm.

The infiltrant may contain adjuvants, which may or may not infiltrate the pits and cracks. The infiltrant for certain reasons may or may not contain known dental fillers in sizes from 1 nanometer to 100 microns, which may or may not infiltrate the pits and cracks.

The infiltrant preferably has a contact angle at room temperature (23° C.) and the given atmospheric pressure in air less than about 60°, more preferably 0 to about 35° on any plane ceramic or soda-lime glass or rather soda-lime-silica glass surface finished with 4000 grit mirror polish. The surface tension of the infiltrant measured at room temperature (23° C.) and the given atmospheric pressure is preferably higher than about 5 mN/m, more preferably higher than about 10 mN/m, and most preferably higher than about 20 mN/m or between about 20 and 50 mN/m.

Surface tensions of infiltrants can be determined, e.g., with a KRÜSS DSA 10 optical drop shape analyzer (KRÜSS GmbH, Germany), e.g., using the pendant drop method.

Contact angles of infiltrants can be measured, e.g., on soda glass slides (e.g., Menzel-Glaser, Thermo Scientific, Gerhard Menzel GmbH, Germany) or polished ceramic discs, e.g., using a KRÜSS DSA 10 optical drop shape analyzer (KRÜSS GmbH, Germany), e.g., using the sessile drop method.

The infiltrant comprises from 90 to 99.9, preferably from 95 to 99.9 percent by weight polymerizable monomers or a mixture of polymerizable monomers, oligomers or pre-polymers. Most preferred is an infiltrant, which comprises of 95 to 99.8 percent of a mixture of monomers comprising at least two polymerizable groups.

Suitable monomers, oligomers and pre-polymers are acrylates and methacrylates or acrylamides and methacrylamides. Preferred polymerizable monomers, oligomers or pre-polymers are crosslinkable monomers, oligomers or pre-polymers. Preferred crosslinkable monomers, oligomers or pre-polymers are diacrylates, triacrylates or polyacrylates or dimethacrylates, trimethacrylates or polymethacrylates or diacrylamides, triacrylamides or polyacrylamides or dimethacrylamides, trimethacrylamides or polymethacrylamides.

Further suitable monomers, oligomers and pre-polymers contain one or more polymerizable moieties selected from the group of a polymerizable double bond and a ring-opening polymerizable group and a thiol group and an epoxide group and a vinyl group.

A preferred composition of an infiltrant for the treatment of a degraded dental ceramic surface in the oral cavity comprises the components (a)-(g) defined below, in which the parts of the components (a)-(g) add to 100. The proportions of the components are given in parts per weight.

Component (a) is a monomer or mixture of monomers containing exactly 2 polymerizable groups per molecule. Preferred are infiltrant compositions comprising component (a) at 30 to 99.5 wt. %. Even more preferably component (a) is comprised at 30 to 79 wt. %, and most preferably component (a) is comprised at 40 to 74 wt. %.

They may preferably be selected from the group consisting of allyl methacrylate; allyl acrylate; PRDMA, 1,3-propanediol dimethacrylate; BDMA, 1,3-butanediol dimethacrylate; BDDMA, 1,4-butanediol dimethacrylate; PDDMA, 1,5-pentanediol dimethacrylate; NPGDMA, neopentyl glycol dimethacrylate; HDDMA, 1,6-hexanediol dimethacrylate; NDDMA, 1,9-nonanediol dimethacrylate; DDDMA, 1,10-decanediol dimethacrylate; DDDDMA, 1,12-dodecanediol dimethacrylate; PRDA, 1,3-propanediol diacrylate; BDA, 1,3-butanediol diacrylate; BDDA, 1,4-butanediol diacrylate; PDDA, 1,5-pentanediol diacrylate; NPGDA, neopentyl glycol diacrylate; HDDA, 1,6-hexanediol diacrylate; NDDA, 1,9-nonanediol diacrylate; DDDA, 1,10-decanediol diacrylate; DDDDA, 1,12-dodecanediol dimethacrylate; EGDMA, ethylene glycol dimethacrylate; DEGDMA, diethylene glycol dimethacrylate; TEDMA, triethylene glycol dimethacrylate; TEGDMA, tetraethylene glycol dimethacrylate; EGDA, ethylene glycol diacrylate; DEGDA, diethylene glycol diacrylate; TEDA, triethylene glycol diacrylate; TEGDA, tetraethylene glycol diacrylate; PEG200DMA, polyethylene glycol 200 dimethacrylate; PEG300DMA, polyethylene glycol 300 dimethacrylate; PEG400DMA, polyethylene glycol 400 dimethacrylate; PEG600DMA, polyethylene glycol 600 dimethacrylate; PEG200DA, polyethylene glycol 200 diacrylate; PEG300DA, polyethylene glycol 300 diacrylate; PEG400DA, polyethylene glycol 400 diacrylate; PEG600DA, polyethylene glycol 600 diacrylate; PPGDMA, polypropylene glycol dimethacrylate; PPGDA, polypropylene glycol diacrylate; NPG(PO)2DMA, propoxylated (2) neopentyl glycol dimethacrylate; NPG(PO)2DA, propoxylated (2) neopentyl glycol diacrylate; bis-MA, bisphenol A dimethacrylate; bis-GMA, bisphenol A glycerol dimethacrylate; BPA(EO)DMA, ethoxylated bisphenol A dimethacrylate (EO=1-30); BPA(PO)DMA, propoxylated bisphenol A dimethacrylate (PO=1-30); BPA(EO)DA, ethoxylated bisphenol A diacrylate (EO=1-30); BPA(PO)DA, propoxylated bisphenol A diacrylate (PO=1-30); BPA(PO)GDA, propoxylated bisphenol A glycerol diacrylate; UDMA, diurethane dimethacrylate; TCDDMA, tricyclo[5.2.1.0]decanedimethanol dimethacrylates; TCDDA, tricyclo[5.2.1.0]-decanedimethanol diacrylates; EBA, N,N'-ethylenebis-acrylamide; DHEBA, N,N'-(1,2-dihydroxyethylene)bisacrylamide; DEPBA, N,N'-diethyl(1,3-propylene)bisacrylamide; TMH-MBMA, N,N'-(2,2,4-trimethylhexamethylene)bismethacrylamide; and bis[2-(2-methylacrylamino)ethoxycarbonyl] hexamethylenediamine.

Component (b) is a monomer or mixture of monomers with at least 3 polymerizable groups in one molecule.

The proportion of crosslinking monomers having at least three polymerizable groups can be between 0% and 60%, preferably 10% and 60%, even more preferably between 20 and 60% and most preferably between 25 and 50% by weight.

Suitable low-viscosity monomers having at least three polymerizable groups are, for example, glycerol triacrylate, TMPTMA, trimethylolpropane trimethacrylate; TMPTA, trimethylolpropane tri(meth)acrylate; DTMPTA, ditrimethylolpropane tetra(meth)acrylate; diPENTA, dipentaerythritol penta(meth)acrylate; or DPEHA, dipentaerythritol hexa (meth)acrylate.

Preferred low-viscosity monomers having at least three polymerizable groups are based for example on alkoxylated multiple alcohols (tri-, tetra-, penta-, hexa-, polyols) such as trimethylolpropane, ditrimethylolpropane, glycerol, pentaerythritol or dipentaerythritol.

Another preferred group of monomers are (meth)acrylic esters of alkoxylated multiple alcohols such as, for example, ethoxylated glycerol triacrylate, propxylated glycerol triacrylate, ethoxylated trimethylolpropane trimethacrylate, ethoxylated trimethylolpropane triacrylate, propoxylated trimethylolpropane trimethacrylate, propoxylated trimethylolpropane triacrylate, ethoxylated pentaerythritol trimethacrylate, ethoxylated pentaerythritol triacrylate, ethoxylated pentaerythritol tetramethacrylate, ethoxylated pentaerythritol tetraacrylate, ethoxylated dipentaerythritol trimethacrylate, ethoxylated dipentaerythritol tetramethacrylate, ethoxylated dipentaerythritol pentamethacrylate, ethoxylated dipentaerythritol hexamethacrylate, ethoxylated dipentaerythritol triacrylate, ethoxylated dipentaerythritol tetraacrylate, ethoxylated dipentaerythritol pentaacrylate, ethoxylated dipentaerythritol hexaacrylate, propoxylated pentaerythritol trimethacrylate, propoxylated pentaerythritol triacrylate, propoxylated pentaerythritol tetramethacrylate, propoxylated pentaerythritol tetraacrylate, propoxylated dipentaerythritol trimethacrylate, propoxylated dipentaerythritol tetramethacrylate, propoxylated dipentaerythritol pentamethacrylate, propoxylated dipentaerythritol hexamethacrylate, propoxylated dipentaerythritol triacrylate, propoxylated dipentaerythritol tetraacrylate, propoxylated dipentaerythritol pentaacrylate and propoxylated dipentaerythritol hexaacrylate.

Those alkoxy groups attached to the alcohols represent (molecular-) chain extenders. Chain extension may be achieved preferably through ethoxylation or propoxylation. For chain extension there are further linking possibilities available, examples being ether bonds, ester bonds, amide bonds, urethane bonds, and the like, which may be followed in turn preferably by ethylene glycol groups or propylene glycol groups.

The chain-extending group is functionalized preferably terminally with the crosslinking groups, preferably with a methacrylate or an acrylate group, a methacrylamide or acrylamide group.

A crosslinking point is regarded as being the position of the crosslinking polymerizable group—for example, the position of a C═C double bond in the monomer.

The chain length is preferably such that the distance between crosslinking points is at least 3, preferably at least 6, more preferably 6 to 30 and more preferably 6 to 26 bond lengths, with particular preference to 6 to 12 bond lengths.

By distance between crosslinking points is meant the shortest distance between the crosslinking groups, as for example two C═C double bonds, along the molecule. The reference is therefore only to the constitution of the molecule, and not, say, to the actual spatial position of the groups relative to one another, as governed, for instance, by configuration or conformation.

By bond length is meant the distance between two atoms in the molecule, irrespective of the nature of the covalent bonding and of the exact length of the individual covalent bond.

The fraction of crosslinking monomers having at least three polymerizable groups and a distance between crosslinking points of less than 30 bond lengths, preferably less than 12 bond lengths, based on the total mass of the monomers, is preferably less more than 10% by weight, more preferably more than 20% by weight, more preferably more than 25% by weight.

Component (c) is a monomer or mixture of monomers with one or more further functional group(s) in one molecule.

Preferably the infiltrant comprises polymerizable monomers selected from the above polymerizable monomers, oligomers a pre-polymers having one or more further functional group(s). Further functional groups are selected from hydroxy group (—OH) or groups containing a hydroxy group. Suitable groups are carboxylic acid groups (—CO—OH), phosphoric acid ester groups (—O—$PO(OH)_2$,), or phosphonic acid groups (—PO(—$OH)_3$) and/or silanol groups (Si—OH) or groups which can be hydrolyzed to yield silanol groups. Most preferred are silanol groups (Si—OH) and groups which can be hydrolyzed to yield silanol groups (Si—OR). Silanol groups can be the —$SiR_2$—OH, —$SiR(OH)_2$ or the —$Si(OH)_3$ group, where R is preferably alkyl and more preferably methyl. Groups which can be hydrolyzed to yield a silanol group are preferably $SiR_{3-n}(X)_n$ groups with n=1-3 and R=alkyl, preferably methyl and X being a hydrolysable group. Polymerizable monomers bearing silanol groups or groups which can be hydrolyzed to yield silanol groups are preferably in their non-hydrolyzed or partially hydrolyzed form. Most preferably the polymerizable silicon containing monomer is methacryloyl oxypropyl trimethoxysilane (MEMO). Preferably the infiltrant comprises 0.1 to 50 percent by weight polymerizable monomers selected from the above polymerizable monomers, oligomers a pre-polymers having one or more further functional group, more preferably 1 to 40 percent by weight, more preferably 3 to 30 percent by weight, most preferably 20 to 30 percent by weight.

In a further embodiment of the invention preferably the infiltrant comprises 3 to 30, preferably 3 to 10 percent by weight polymerizable monomers selected from the above polymerizable monomers, oligomers a pre-polymers having one or more further functional group.

Phosphonic and phosphoric acid groups are preferred acid groups. Examples include corresponding organic hydrogenphosphates or dihydrogenphosphates.

The acid-group-containing monomers may be of crosslinking construction—that is, in addition to the acid group, the monomer molecule contains two or more polymerizable groups.

In selected applications it may be advantageous if the polymerizable monomers, oligomers and pre-polymers having one or more further functional group(s) contain only one polymerizable group. The acid-group-containing monomers may more particularly be acrylates or methacrylates, acrylamides or methacrylamides.

For example, they may be acrylates or methacrylates which are listed later on below as preferred additional monomers having a polymerizable group, which also have a corresponding acid group.

In accordance with the invention the acid-group-containing monomers preferably have a molecular weight (weight average) of 100-1000 g/mol. The acid-group-containing monomers are preferably soluble in the infiltrant. The term "nonaqueous" here denotes preferably infiltrants which contain less than 5% by weight, preferably less than 2% by weight, of water.

Acid-group-containing monomers which can be used with preference are, for example, 4-methacryloyloxyethyl-trimellitic acid (4-MET), methacryloyloxydecylmalonic acid (MAC-10), maleic acid mono-HEMA ester, N-methacryloyl-N',N'-dicarboxymethyl-1,4-diaminobenzene, N-2-hydroxy-3-methacryloyloxypropyl-N-phenylglycine, O-methacryloyltyrosinamide, 4-methacryloylaminosalicylic acid, phenyl methacryloyloxyalkylphosphates, e.g., phenyl methacryloyloxyethyl phosphate (phenyl-P), methacryloyloxyalkyl dihydrogenphosphates, e.g., methacryloyloxyethyl dihydrogenphosphate (HEMA-P), methacryloyloxypropyl dihydrogenphosphate (MPP), methacryloyloxyhexyl dihydrogenphosphate (MHP), methacryloyloxydecyl dihydrogenphosphate (MDP), glyceryl dimethacrylate phosphate (GPDM), pentaerythritol triacrylate phosphate (PENTA-P), bis(hydroxyethyl methacrylate)phosphate, (meth)acryl-amidophosphates, (meth)acrylamidodiphosphates, (meth)acrylamidoalkyl phosphonates, (meth)acrylamidoalkyl diphosphonates, bismethacrylamidoalkyl dihydrogenphosphates, vinylbenzylphosphonic acid, and vinylbenzoic acid.

Among the stated methacryloyloxyalkyl dihydrogenphosphates, particular preference is given to methacryloyloxydecyl dihydrogenphosphate (MDP).

The acid component (c1) is preferably present in an amount of 0.5-10 wt. % and more preferably in an amount of 0.5-5 wt. % based on the entire infiltrant.

Preferred polymerizable monomers, oligomers or prepolymers having one or more further functional group(s) are mentioned above. As component (c2) the infiltrant preferably comprises polymerizable monomers selected from monomers bearing silanol groups (Si—OH) or groups which can be hydrolyzed to yield silanol groups with the definitions shown above. Component (c2) is preferably present in an amount of 0.5 to 25 wt %, more preferably 0.5 to 20 wt. % and most preferably 1 to 10 wt. %.

Component (d) is an initiator.

The infiltrant comprises 0.05 to 10% by weight infiltrant-soluble initiators for the light induced radical polymerization (photoinitiators). The infiltrant may comprise 0.05 to 9.9% by weight infiltrant-soluble accelerators for the light induced radical polymerization. Suitable initiators preferably operate in the wavelength region from 300 to 600 nm, more preferably in the region from 350 to 500 nm, most preferably from 400 to 500 nm. Preferred initiators are camphorquinone (CQ), bisacylphosphine oxide (BAPO), trimethylbenzoyl-diphenyl-phosphine oxide (TPO) and thioxanthone derivatives. The selection of suitable accelerators depends on the selected initiator, which is in no way a challenge for the expert.

The term initiator system should be understood as a combination of a photoinitiator and an appropriate accelerator or group of accelerators.

Component (e)

The infiltrant optionally comprises up to 10% by weight of infiltrant-soluble additives. Suitable additives are common additives for polymerizable dental materials known in the art, like stabilizers, infiltrant soluble fluorescent and other dyes etc. Further suitable additives are polymers like poly (meth)acrylates.

Component (f)

The infiltrant may comprise up to 10 percent by weight of known solvents, which exhibit no polymerizable group. The solvent may help to dilute higher molecular monomers or oligomers, such as UDMA and BisGMA in the infiltrant. Preferred are low molecular alcohols, ethers and ketones or mixtures thereof. Preferably the infiltrant comprises however no such organic solvent, which exhibit no polymerizable group. The infiltrant comprises less than 1 percent by weight water or preferably no or only unavoidable traces of water.

In a preferred embodiment the infiltrant comprises at least the components (a) to (d). In another embodiment the infiltrant comprises (a), (b), (c2) and (d). In yet another embodiment the infiltrant comprises the components (a), (b), (c1) and (d). In a preferred embodiment the infiltrant comprises the components (a), (b), (c1, c2) and (d).

The infiltrant components (a)-(d) bear (meth)acrylate or (meth)acrylamide groups as polymerizable groups with (meth)acrylate groups being most preferred.

It is preferred that apart from functional group containing monomers the composition of this invention does comprises no major concentrations of polymerizable monomers bearing only one polymerizable group on the molecule. The amount of such monomers should be less than 20 wt. % and more preferably less than 5 wt. %. It is particularly preferred that the composition of the present invention does not contain such monomers.

Methods

Viscosity

The dynamic viscosity of the infiltrants might be measured by any suitable method. Suitable measurement methods of the dynamic viscosities of the infiltrants are further described in the Examples.

Surface Roughness

The surface roughness might be measured by any suitable method. The evaluation of the surface roughness (Ra) was conducted using an optical confocal profilometer (high-resolution non-contact confocal white-light profilometer; CyberSCAN CT 100, Cyber Technologies GmbH, Germany). The surface area of the specimens was scanned with a 0.02 mm resolution sensor head in 10 μm step-sizes for 0.5 ms illumination time each. In this technique, the height levels are detected over a measurement range defined by different wavelengths within the projected white light beam spectrum. Changes regarding intensity and wavelength are analyzed by the spectrometer, which defines height levels as they reach the maximum intensity level for a specific wavelength. Reflection intensities were selected to prevent interference from sub-surface signals for a clean reading of light reflections coming uniquely from the surface.

Adhesion

Ceramic bars were cut from Vitablocs Mark II using a diamond saw (Buehler) and grinded with a diamond wheel to the testing dimensions (3×3×13 mm and 3×6×13 mm). The infiltrants were applied on both opposing surfaces, which were brought together and polymerized for 20 s from two different sides using a light curing unit (Elipar Trilight, 3M ESPE) at a light intensity of 800 $mW/cm^2$. The samples were stored dry at room temperature. The tensile test was carried out in air using a universal testing machine (Z 2.5, Zwick, Ulm, Germany) with a crosshead speed of 1 mm/min by pulling the top bar using a low compliance rope (Dyneema SK75, DSM Dyneema, Stanley, USA) until debonding. The tensile bond strengths were calculated by dividing the maximum applied load (N) by the rectangular area of the adhesive interface, measured with a digital caliper after test.

Biaxial Flexural Strength

The Biaxial flexural strength might be measured by any suitable method.

Method 1

After 24 h of water storage, the specimens from the control group (polished, n=15) and the experimental groups (ground/polished, indented and sandblasted, n=15) were tested in flexure using the piston-on-three-balls set-up, according to the ASTM F 394-78 standard. The test was conducted in a universal testing machine (Zwick 2.5, Zwick, Germany) at a cross-head speed of 0.75 mm/min until fracture in air.

Method 2

After storage in a dry environment at room temperature the specimens from the control group (polished, n=15) and the experimental group (sandblasted, n=15) were tested in flexure using the piston-on-three-balls set-up, according to the ASTM F 394-78 standard. The test was conducted in a universal testing machine (Zwick 2.5, Zwick, Germany) at a cross-head speed of 1 mm/min until fracture in air.

EXAMPLES

The following substances were used in the examples

| Substance | Abbreviation |
|---|---|
| Triethylene glycol dimethacrylate (Evonik, Germany; η~10 mPa * s at RT) | TEDMA |
| 1,6-Hexanediol dimethacrylate (Esstech, US) | HDDMA |
| Diurethane dimethacrylate, mixture of isomers, CAS 72869-86-4 (Genomer ® 4297, Rahn, Switzerland) | UDMA |
| Bisphenol A glycerolate dimethacrylate, CAS 1565-94-2 (CCP Composites, US) | BisGMA |
| Ethoxylated $(EO)_3$ trimethylolpropane triacrylate (Miramer ® 3130, Rahn, Switzerland, η~60 mPa * s at RT) | ETMPTA |
| Trimethylolpropane trimethacrylate (Visiomer ® TMPTMA, Evonik, Germany) | TMPTMA |
| 3-(Trimethoxysilyl) propyl methacrylate (Dynasylan ® MEMO, Evonik, Germany, η~3 mPa * s at RT) | MEMO |
| 10-Methacryloyl-oxydecyl-dihydrogenphosphate | MDP |
| Camphorquinone (Rahn, Switzerland) | CQ |
| 2-Ethylhexyl-p-dimethylaminobenzoate (Genocure ® EHA, Rahn, Switzerland) | EHA |
| Butylated hydroxytoluene | BHT |
| Ethyl-p-dimethylamino benzoate, 99% purity, Alfa Aesar | EDAB |
| Poly(methyl methacrylate), Degacryl MW 332, Evonik Industries, | PMMA |

Preparatory Example 1

In a light protected glass container 59.2 parts per weight TEDMA, 14.8 parts per weight ETMPTA, 0.5 parts per weight CQ, 0.8 parts per weight EHA and 0.0015 parts per weight BHT were mixed and the mixture was stirred at ambient temperature by means of a magnetic stirrer until a homogeneous clear solution was obtained. This solution was kept at room temperature under exclusion of light (which may cause curing). In a light protected glass container 75 parts per weight of the solution were mixed with 25 parts per weight of MEMO by means of a magnetic stirrer until a clear and homogeneous solution was obtained. Thereafter this infiltrant was used for the treatment of damaged ceramic surfaces.

The viscosity of the infiltrant was measured using a Malvern Kinexus Rheometer (Malvern Instruments GmbH, Germany) equipped with a coaxial cylinder device for the measurement of liquids according to DIN 53019 with a cone of 25 mm in diameter in a cylinder of 27 mm diameter at a temperature of 23° C. A volume of approximately 18 ml of the infiltrant was used in the cylinder. The measurement was made under exclusion of ambient light to prevent polymerization. The following parameters were applied: Table of shear stresses from 0.1 Pa to 1 Pa. The viscosity value at 0.126 Pa shear stress was taken. The viscosity of the infiltrant was 6.2 mPa·s.

Preparatory Examples 2 to 7

In a light protected glass container under yellow light conditions for each preparatory example substances were mixed as specified in Table 2 and the mixtures were stirred at ambient temperature by means of a magnetic stirrer until homogeneous clear solutions were obtained. The solutions were kept at room temperature under exclusion of light until the infiltrants were used for the treatment of damaged ceramic surfaces.

The viscosity of the infiltrants was measured using a dynamic plate/plate viscometer (DSR, Dynamic Stress Rheometer, Rheometric Scientific, Inc., US). Measurements took place in steady stress sweep mode with slot sizes of 0.1 to 0.5 mm in the range from 0 to 50 Pa shear stress without preliminary shearing of the infiltrants. The viscosity of the infiltrants is given in Table 1.

TABLE 1

Compositions prepared in the preparatory examples; values given in parts per weight; viscosity of the samples according to the method described.

| | Preparatory Example | | | | | | |
|---|---|---|---|---|---|---|---|
| Substance | 1 | 2 | 3 | 4 | 5 | 6 | 7 |
| TEDMA | 59.2 | 32.0 | 28.8 | 30.4 | 28.83 | 22.4 | 22.4 |
| HDDMA | — | 57.5 | 51.34 | 54.5 | 51.69 | 40.1 | 40.1 |
| UDMA | — | — | — | — | — | — | — |
| BisGMA | — | — | — | — | — | — | — |
| ETMPTA | 14.8 | 8.0 | 7.2 | 7.6 | 7.21 | 30.0 | — |
| TMPTMA | — | — | — | — | — | — | 30.0 |
| MDP | — | — | 5.1 | 5.0 | 5.0 | 5.0 | 5.0 |
| MEMO | 25 | — | 5.0 | — | — | — | — |
| CQ | 0.5 | 0.5 | 0.5 | 0.5 | 0.5 | 0.5 | 0.5 |
| EHA | 0.8 | — | — | — | — | — | — |
| EDAB | — | 2.0 | 2.0 | 2.0 | 2.0 | 2.0 | 2.0 |
| BHT | 0.0015 | 0.002 | 0.003 | 0.003 | 0.002 | 0.002 | 0.002 |
| PMMA | — | — | — | — | 4.76 | — | — |
| Viscosity/ mPa · s | 6.2 | 7.1 | 8.9 | 9.1 | 56.4 | 13.7 | 11.8 |

Example 1—Healing of Damaged Dental Ceramic Surface Using an Infiltrant

Ceramic specimen (disks, Ø=12.5 mm and 1.2 mm in thickness) were produced using a glass-ceramic powder material (VM9, Vita Zahnfabrik) by condensation and sintering. Sintering was conducted in an oven (Vacumat 4000, Vita Zahnfabrik) according to the following program: 55° C./min heating rate, holding time of 1 min at 940° C. under vacuum and cooling rate of 30° C./min. The sintered discs were reduced to the final thickness by grinding with a diamond wheel and subsequently mirror polished with SiC papers (Buehler) from 320, 600, 100, 1200, 2500 down to 4000 grit on the side subjected to tension.

Specimens of the experimental groups were further prepared according to two surface treatments: (i) bur treatment with a coarse diamond bur (Komet bur #220) at 2500 rpm for 10 s with air cooling; (ii) sandblasted with 35 μm-sized aluminum oxide particles at 2 bar pressure for 10 s in an angle of 45°. An optical confocal profilometer was used to measure the mean roughness (Ra) of treated samples, which resulted in Ra=30 μm for the grinded specimens, and Ra=5 μm for the sandblasted specimens. The damaged surfaces were subsequently infiltrated.

The infiltrant was applied twice with a micro brush onto the ceramic surface and left untouched for 30 s. After this time the infiltrant was removed from the surface using a cotton pellet, leaving the surface shiny. Subsequently, the infiltrated ceramic surface was light-cured, using a halogen blue-light lamp (Elipar Trilight, 3M ESPE) for 2×40 s at a light intensity of 800 $mW/cm^2$. Light intensity was periodically controlled with a radiometer. After light-curing the ceramic discs were stored in vials containing distilled water, sealed and stored in a heating module at 37° C.

After 24 h of water storage, the specimens from the control group (polished, n=15) and the experimental groups (grinded and sandblasted, n=15) were tested in flexure using the piston-on-three-balls set-up, according to the ASTM F 394-78 standard. The test was conducted in a universal testing machine (Zwick 2.5, Zwick, Germany) at a crosshead speed of 0.75 mm/min until fracture in air.

Mean roughness (Ra) values for bur-treated and sandblasted samples were 30 μm and 5 μm, respectively. Shape and scale parameters for the Polished samples were as follows: m=10.3 and $\sigma_0$=101.2 MPa. For Bur-treated samples: m=7.6 and $\sigma_0$=66.4 MPa for Bur Control; m=9.0 and $\sigma_0$=84.2 MPa for Bur Infiltrated. For Sandblasted samples: m=12.6 and $\sigma_0$=78.2 MPa for Sandblasted Control; m=8.8 and $\sigma_0$=99.98 MPa for Sandblasted Infiltrated. The increase in $\sigma_0$ after infiltration was significant at a 95% level for both Bur-treated and Sandblasted samples. The infiltration of smaller defects (Sandblasted samples) restored the strength to the level of the polished control, being more efficient than infiltration of larger defects (Bur-treated samples).

The infiltration of defects created by coarse bur or sandblasting has shown to increase the strength of dental ceramics in comparison to non-infiltrated damaged ceramic samples. The infiltration of small defects may restore the strength of dental ceramics to its initial values. The infiltration of damaged areas, whether created by the dentist during intra-oral adjustments or during function, has the potential to increase the lifetime of dental ceramic prostheses by delaying crack growth and fracture.

Example 2—Surface Crack Healing With Infiltrants: Glass Versus Feldspathic Ceramics As comparison specimen Soda-lime glass discs (0=15 mm and 1.9 mm in thickness; Schott, Germany) were used. A Vickers indent (Zwick, Germany) was produced on the tensile side of the ceramic discs from example 1 and the Soda-lime glass discs (1 kg during 15 s for VM9 and 500 g during 15 s for glass). Infiltration was carried out as described in Example 1.

After 24 h of water storage, the discs were tested in flexure using the piston-on-three-balls set-up. Weibull parameters m and $\sigma_0$ were calculated (n=15 for VM9 and n=10 for glass) and mathematically corrected according to the n number. The infiltration depth into the Vickers indent was measured in samples infiltrated with a fluorescent dyed-infiltrant using a confocal laser scanning microscope (TCS SL, Leica, Germany).

Shape and scale parameters for the Glass samples were as follows: m=7.0 and $\sigma_0$=335.9 MPa for Polished; m=5.9 and $\sigma_0$=106.8 MPa for Indented; m=8.2 and $\sigma_0$=223.2 MPa for Infiltrated. Shape and scale parameters for the Ceramic VM9 samples were as follows m=10.3 and $\sigma_0$=101.2 MPa for Polished; m=11.4 and $\sigma_0$=63.52 MPa for Indented; m=5.1 and $\sigma_0$=83.9 MPa for infiltrated. The increase in $\sigma_0$ after infiltration was significant at a 95% level for both Glass and Ceramic. Infiltration depth in glass samples was recorded up to 18 μm in depth, while in ceramics the infiltration depth was 2-4 μm in depth (subsurface layer).

As in glass, the infiltration of surface cracks with low-viscosity infiltrants and subsequent hardening is able to strengthen veneering ceramics and potentially prevent chipping events. The infiltration depth in ceramics is limited but does not seem to hinder its reinforcing effect.

The results of Example 1 and Example 2 are summarized in Table 2.

TABLE 2

Biaxial flexural strengths of sintered ceramic discs and soda lime glass discs of Examples 1 and 2 with different pretreatments of the glass/ceramic surface. Infiltration of the surface was performed using the infiltrant from preparatory example 1.

| | Example 1 | | | | | | | Example 2 | | |
|---|---|---|---|---|---|---|---|---|---|---|
| | Feldspar glass ceramic disks | | | | | | | Soda lime glass disks | | |
| | P | S | SI | B | BI | I | II | W | I | II |
| Mean roughness [μm] | | 5 | | 30 | | | | | | |
| Weibull - m | 10.3 | 12.6 | 8.8 | 7.6 | 9.0 | 11.4 | 5.1 | 7.0 | 5.90 | 8.20 |
| Weibull - $\sigma_0$ [MPa] | 101.2 | 78.2 | 100.0 | 66.4 | 84.2 | 63.5 | 83.9 | 335.9 | 106.8 | 223.2 |

P—polished 4000 grit,
S—sandblasted,
SI—sand-blasted and infiltrated,
B—bur treated,
BI—bur treated and infiltrated,
I—indented,
II—indented and infiltrated,
W—without treatment

Example 3—Healing of Dental Ceramic Surfaces Damaged by Sandblasting Using the Infiltrants of Preparatory Examples 2-7

Ceramic plates (12×12 mm) were cut from fine structured feldspar ceramic blocks (Vitablocs® Mark II, Vita, Germany) and reduced to the final thickness (1.3±0.05 mm) by grinding with a diamond wheel as described in Example 1.

The ceramic plates were subjected to two different surface treatments:

(i) mirror polished with SiC papers (Buehler) down to 4000 grit on the side subjected to tension and;

(ii) sandblasted with 35 μm-sized aluminum oxide particles at 2 bar pressure for 5 s in an angle of 45°.

Each infiltrant was applied once with a microbrush onto the ceramic surface and left untouched for 30 s. After this time the infiltrant was removed from the surface using a cotton pellet, leaving the surface shiny. Subsequently, the infiltrated ceramic surface was light-cured, using a halogen blue-light lamp (Unilux AC Kulzer) for 1×60 s at a light intensity of 800 mW/cm$^2$. After light-curing, the infiltrated samples were stored dry at room temperature. The specimens from the control group (polished, n=15) and the experimental group (sandblasted, n=15) were tested in flexure using the piston-on-three-balls set-up according to the method 2 described above. The results of Example 3 are summarized in Table 3.

TABLE 3

Biaxial flexural strengths of sandblasted ceramic discs of example 3 treated with infiltrants of the respective preparatory examples; comparison with polished discs and sandblasted discs not treated with an infiltrant. Example 3

| | Feldspar glass ceramic disks | | | | | | | |
|---|---|---|---|---|---|---|---|---|
| | | | Sandblasted and infiltrated Preparatory Example No. | | | | | |
| | polished | sand blasted | 2 | 4 MDP | 3 MEMO | 5 PMMA | 6 TA | TM |
| Biaxial flexural strength [MPa] | 113.6 | 104.7 | 128.3 | 123.4 | 127.4 | 125.7 | 137.4 | 14 |

Example 4—Adhesion Test of Infiltrant on Ceramic

To test the adhesion of infiltrants to feldspatic porcelain the adhesion test described above was applied. The results are summarized in Table 4.

TABLE 4

Adhesion of infiltrants to Feldspatic ceramic rods in tensile testing

| | Preparatory example No. | | |
|---|---|---|---|
| | 3 | 4 | 7 |
| Adhesion/MPa | 6.8 | 4.7 | 4.4 |

Examples show that the degradation of the surface either by sandblasting or by indenting the ceramic surface yield marked deteriorations of the mechanical properties of the ceramic bodies (derived from biaxial flexural strength). The applied surface degradation methods serve as models for the intraoral degradation of ceramic restorations.

The infiltration of the surface degraded specimens in Examples 1 and 2 results in improved mechanical properties up to the mechanical properties of the mirror polished original specimens.

Using the infiltrants of example 3 (preparatory examples no. 2-7) yields mechanical properties even superior to the polished control.

Particularly compositions containing extremely high amounts of monomers bearing two or three polymerizable groups in the molecule (preparatory examples no. 6 and 7) used as infiltrants for the ceramic surface show the highest reinforcing effect.

From the data of example 4 it can be derived that the addition of a silane and an acid is preferred. Thereby the addition of only small amounts of silanes like MEMO and acids like MDP is preferred, in order to not decrease the amount of monomers bearing two or in particular three polymerizable groups in the molecule to an undesirably low extend.

A higher durability and a greater potential for the stabilization of roughened dental ceramic surfaces can be expected in particular from ceramic infiltrants containing high amounts of crosslinkable Monomers comprising at least three polymerizable groups and lower amounts of monomers comprising a silanol group.

The invention claimed is:

1. A method for strengthening a fixed ceramic dental prosthesis in the oral cavity comprising the following steps:

a) drying of a ceramic surface layer, b) applying onto the dried ceramic surface layer an infiltrant comprising from 90 to 99.9 wt.-% of at least one polymerizable monomer, oligomer or prepolymer and from 0.05 to 10 wt.-% of a polymerization initiator, the infiltrant having a dynamic viscosity of 0.3 to 100 mPa·s (23° C.), and c) curing the infiltrant in the ceramic surface layer.

2. The method of claim 1, wherein drying of the ceramic surface layer is by purging said ceramic surface layer with an organic solvent having an Evaporation Index of 1 to 35.

3. The method of claim 2, wherein said organic solvent has an Evaporation Index of 1 to 15.

4. The method of claim 1, wherein prior to drying said ceramic surface layer, said ceramic surface layer of said fixed prosthesis is cleaned and/or rinsed.

5. The method of claim 1, wherein after applying said infiltrant, the method comprises cleaning the surface of the ceramic surface layer from adherent infiltrant.

6. The method of claim 1, wherein after curing said infiltrant in said ceramic surface layer, said method comprises cleaning and/or polishing the surface of the ceramic surface layer.

7. The method of claim 1, wherein said infiltrant has a dynamic viscosity of 0.3 to 60 mPa·s (23° C.).

8. The method of claim 7, wherein said infiltrant has a dynamic viscosity of 0.3 to 30 mPa·s (23° C.).

9. The method of claim 7, wherein said infiltrant has a dynamic viscosity of 2 to 15 mPa·s (23° C.).

10. The method of claim 1, wherein said infiltrant comprises 3-30 wt. % of polymerizable monomers, oligomers or pre-polymers having one or more further functional group(s) selected from:

a) hydroxy group (—OH), b) groups containing a hydroxy group, c) silanol groups (Si—OH), d) groups which can be hydrolyzed to yield silanol groups.

11. The method of claim 10, wherein said groups containing a hydroxy group are selected from the group consisting of carboxylic acid groups (—CO—OH), phosphoric acid ester groups (—O—PO$(OH)_2$), and phosphonic acid groups (—PO(—$OH)_3$).

12. The method of claim 10, wherein said infiltrant comprises at least 65 wt.-% of polymerizable monomers, oligomers or pre-polymers having 2 or more polymerizable groups.

13. The method of claim 12, wherein said infiltrant comprises:

a) 45 to 75 wt.-% of polymerizable monomers, oligomers or pre-polymers having 2 polymerizable groups, b) 20 to 50 wt.-% of polymerizable monomers, oligomers or pre-polymers having 3 or more polymerizable groups c) 3-30 wt.-% of polymerizable monomers, oligomers or pre-polymers having one or more further functional group(s) selected from:

i) hydroxy group (—OH), ii) groups containing a hydroxy group, iii) silanol groups (Si—OH), and iv) groups which can be hydrolyzed to yield silanol groups.

14. The method of claim 13, wherein said groups containing a hydroxy group are selected from the group consisting off carboxylic acid groups (—CO—OH), phosphoric acid ester groups (—O—PO$(OH)_2$), and phosphonic acid groups (—PO(—$OH)_3$).

15. The method of claim 13, wherein said infiltrant comprises:

a) 2.5-9.5 wt.-% of polymerizable monomers, oligomers or pre-polymers having one or more silanol groups (Si—OH), or groups which can be hydrolyzed to yield silanol groups, and b) 0.5-7.5 wt.-% of polymerizable monomers, oligomers or pre-polymers having one or more carboxylic acid groups (—CO—OH), phosphoric acid ester groups (—O—$PO(OH)_2$) or phosphonic acid groups (—PO(—$OH)_3$).

* * * * *